US010781481B2

(12) United States Patent
    Fu

(10) Patent No.: US 10,781,481 B2
(45) Date of Patent: Sep. 22, 2020

(54) MIRNA TRANSCRIPTOME METHODS AND COMPOSITIONS

(71) Applicant: Bio-Rad Laboratories, Inc., Hercules, CA (US)

(72) Inventor: Rongdian Fu, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 193 days.

(21) Appl. No.: 15/499,734

(22) Filed: Apr. 27, 2017

(65) Prior Publication Data

US 2017/0314017 A1    Nov. 2, 2017

Related U.S. Application Data

(60) Provisional application No. 62/328,504, filed on Apr. 27, 2016.

(51) Int. Cl.
| | |
|---|---|
| *C12Q 1/68* | (2018.01) |
| *C12Q 1/686* | (2018.01) |
| *C12N 15/10* | (2006.01) |
| *C12Q 1/6876* | (2018.01) |
| *C12N 15/66* | (2006.01) |
| *C12Q 1/6806* | (2018.01) |

(52) U.S. Cl.
CPC ......... *C12Q 1/686* (2013.01); *C12N 15/1096* (2013.01); *C12N 15/66* (2013.01); *C12Q 1/6806* (2013.01); *C12Q 1/6876* (2013.01); *C12Q 1/68* (2013.01); *C12Q 2600/106* (2013.01); *C12Q 2600/158* (2013.01); *C12Q 2600/178* (2013.01)

(58) Field of Classification Search
CPC ........ C12Q 2521/313; C12Q 2525/191; C12Q 1/6806; C12Q 1/68; C12Q 1/686; C12Q 1/6876; C12Q 2600/106; C12Q 2600/158; C12Q 2600/178; C12N 15/1096; C12N 15/66
USPC ...................................................... 435/91.2
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,962,271 A | 10/1999 | Chenchik et al. | |
| 2004/0002104 A1 | 1/2004 | Fischer et al. | |
| 2009/0005252 A1 | 1/2009 | Drmanac et al. | |
| 2012/0316074 A1* | 12/2012 | Saxonov ................ | C12N 15/10 506/2 |
| 2016/0060674 A1 | 3/2016 | Patel | |
| 2016/0177380 A1* | 6/2016 | Ruan .................... | C12Q 1/6806 506/2 |

FOREIGN PATENT DOCUMENTS

| | | |
|---|---|---|
| WO | 2000/053806 A1 | 9/2000 |
| WO | 2004/099445 A1 | 11/2004 |
| WO | 1584677 A1 | 10/2005 |
| WO | 2007/091077 A1 | 8/2007 |
| WO | 2009/012644 A1 | 1/2009 |
| WO | 2009/082488 A2 | 7/2009 |
| WO | 2012/149042 A2 | 11/2012 |

OTHER PUBLICATIONS

James Schiemer., http://tucf-genomics.tufts.edu/documents/protocols/TUCF_Understanding_Illumina_TruSeq_Adapters.pdf, pp. 105, (Year: 2011).*
Prediger, Integrated DNA technologies, pp. 1-2, published Jan. (Year: 2014).*
Möncke-Buchner, E. et al.; *Journal of Molecular Biology*; vol. 387, No. 5; 2009; pp. 1309-1319.
Meisel, A. et al.; "Type III restriction enzymes need two inversely oriented recognition sites for DNA cleavage"; *Nature*; vol. 355, No. 6359; Jan. 30, 1992; pp. 467-469.
Mucke, M., et al.; *Journal of Molecular Biology*; vol. 312, No. 4; 2001; pp. 687-698.
Pfeffer, S. et al.; *Nat. Meth.*; vol. 2; 2005; pp. 269-276.
New England Biolabs EcoP15I Restriction Enzyme; www.neb.com/products/r0646-ecop15i.html; downloaded from the internet Jun. 22, 2017; 2 pages.
Illumina TruSeq Small RNA Library Preparation Kit; www.illumina.com/products/by-type/sequencing-kits/library-prep-kits/truseq-small-rna.html; downloaded from the internet Jun. 22, 2017; 3 pages.
International Search Report and Written Opinion from PCT/US2017/029831 dated Jul. 18, 2017; 10 pages.
Cheng, J. et al.; "A Molecular Chipper technology for CRISPR sgRNA library generation and functional mapping of noncoding regions"; *Nature Communications*; vol. 7, No. 11178; Mar. 30, 2016; pp. 1-10.
Extended European Search Report in EP Application No. 17790425.7 dated Nov. 4, 2019; 13 pages.

(Continued)

*Primary Examiner* — Cynthia B Wilder
(74) *Attorney, Agent, or Firm* — Kilpatrick Townsend and Stockton LLP

(57) ABSTRACT

Methods, polynucleotides, kits, and reaction mixtures are disclosed for the enriching of short polynucleotide molecules that have a length within a desired target length range. A Type IIS or Type III restriction enzyme is used to cleave polynucleotides at cleavage sites located at a distance from the restriction enzyme recognition sites. For example, a mixture of polynucleotides can be formed by inserting DNA molecules between a recognition site for the restriction enzyme and a region of non-naturally-occurring nucleotides that block cleavage by the restriction enzymes. If a polynucleotide contains a DNA molecule with a length within a target range, then the cleavage site will be within the blocking region, and cleavage will not occur. Polynucleotides containing DNA molecules with lengths outside the target range can be cleaved. By selectively enriching, through PCR or other means, polynucleotides that are intact, a concentrated population of polynucleotides of a target length can be formed.

14 Claims, 8 Drawing Sheets

Specification includes a Sequence Listing.

(56) References Cited

OTHER PUBLICATIONS

Gupta, Y. K. et al.; "Structural basis of asymmetric DNA methylation and ATP-triggered long-range diffusion by EcoP15I"; *Nature Communications*; vol. 6; Jun. 12, 2015; p. 7363.

Matsumura, H. et al.; "Gene Expression Analysis of Plant Host-Pathogen Interactions by Supersage"; *Proceedings of the National Academy of Sciences* (*PNAS*); vol. 100, No. 26; Dec. 23, 2003; pp. 15718-15723.

Wyszomirski, K. H. et al.; "Type III restriction endonuclease EcoP15I is a heterotrimeric complex containing one Res subunit with several DNA-binding regions and ATPase activity"; *Nucleic Acids Research*; vol. 40, No. 8; Apr. 2012; pp. 3610-3622.

\* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: 3'-adaptor containing an EcoP15I binding site
      as shown in FIG. 9
<220> FEATURE:
<221> NAME/KEY: Unsure
<222> LOCATION: (7)..(20)
<223> OTHER INFORMATION: Undefined

<400> SEQUENCE: 1
ctgctgnnnn nnnnnnnnnn                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: Unsure
<222> LOCATION: (1)..(14)
<223> OTHER INFORMATION: Undefined
<220> FEATURE:
<221> NAME/KEY: misc_feature
<222> LOCATION: (15)..(20)
<223> OTHER INFORMATION: EcoP15I

<400> SEQUENCE: 2
nnnnnnnnnn nnnncagcag                                                   20
```

MIRNA TRANSCRIPTOME METHODS AND COMPOSITIONS

CROSS-REFERENCES TO RELATED APPLICATIONS

This application claims the benefit of U.S. Provisional Application No. 62/328,504, filed Apr. 27, 2016, which is incorporated by reference in its entirety herein for all purposes.

REFERENCE TO A "SEQUENCE LISTING" SUBMITTED AS ASCII TEXT FILES VIA EFS-WEB

The Sequence Listing written in file 094260-112010US-1047345 SequenceListing.txt created on Jun. 14, 2017, 1,000 bytes, machine format IBM-PC, MS-Windows operating system, in accordance with 37 C.F.R. 1.821 to 1.825, is hereby incorporated by reference in its entirety for all purposes.

BACKGROUND

Small RNAs are a category of RNA molecules that are typically less than 250 nucleotides in length and do not code for translation into a protein. These molecules often play a regulatory role within the cell, interacting with coding RNAs to affect their translation. Example types of such small RNAs include but are not limited to miRNA, snoRNA, and piRNA.

An miRNA is a single-stranded non-coding RNA molecule containing approximately 22 nucleotides and functioning in the regulation of post-transcriptional gene expression and gene silencing. As a result of this activity, the profiling of miRNA populations is an important tool in the study of, for example, gene regulation, disease development, molecular diagnostics, and pharmacogenetics.

To profile a transcriptome population of miRNA molecules through, for example, miRNA-seq, miRNA RT-qPCR, or miRNA microarrays, the miRNA present in a biological sample frequently must be enriched using a technique such as size-selection gel electrophoresis. Alternatives for producing miRNA libraries include the use of miRNA-specific amplification reactions or hybridization probes. These and other options for enriching miRNA or other small polynucleotides can often be time consuming or difficult to apply to small samples, such as those derived from a single cell.

BRIEF SUMMARY

In general, provided herein are methods, kits, and materials for the enriching of short polynucleotide molecules that have a length within a target range.

One provided polynucleotide comprises a DNA sequence, a first adaptor oligonucleotide comprising a number of contiguous non-naturally-occurring nucleotides, and a second adaptor oligonucleotide comprising a recognition site for a Type IIS or Type III restriction enzyme. The first and second adaptor oligonucleotides are linked to opposite ends of the DNA sequence. The number of contiguous non-naturally occurring nucleotides is sufficient to block cleavage by the Type IIS or Type III restriction enzyme if the DNA sequence has a length within a target length range.

In some embodiments, the DNA sequence has a length within a target range.

In some embodiments, the DNA sequence has a length less than the minimum of the target length range or greater than the maximum of the target length range.

In some embodiments, the DNA sequence comprises a cDNA

In some embodiments, the DNA sequence comprises a cDNA formed through reverse transcription of miRNA.

In some embodiments, the DNA sequence comprises a cDNA formed through reverse transcription of siRNA.

In some embodiments, the recognition site is for a Type IIS restriction enzyme.

In some embodiments, the recognition site is for a Type III restriction enzyme.

In some embodiments, the Type III restriction enzyme is EcoP15I.

In some embodiments, the first or second adaptor oligonucleotide comprises at least one ribonucleotide.

In some embodiments, the number of contiguous non-naturally-occurring nucleotides is between 3 and 20.

In some embodiments, the non-naturally-occurring nucleotides comprise phosphorothioated bases.

In some embodiments, the target length range is between 18 and 24 base pairs.

In some embodiments, the first and second adaptor oligonucleotide each further comprise a primer binding site.

One provided kit for enriching for short polynucleotide sequences from a sample comprises a Type IIS or Type III restriction enzyme, and a first adaptor oligonucleotide comprising a number of contiguous non-naturally-occurring nucleotides.

In some embodiments, the kit further comprises a second adaptor oligonucleotide comprising a recognition site for the Type IIS or Type III restriction enzyme.

In some embodiments, the kit further comprises an RNA ligase.

In some embodiments, the RNA ligase is T4 RNA Ligase 2, Deletion Mutant.

In some embodiments, the kit comprises a Type IIS restriction enzyme.

In some embodiments, the kit comprises a Type III restriction enzyme.

In some embodiments, the Type III restriction enzyme is EcoP15I.

In some embodiments, the first or second adaptor oligonucleotide comprises at least one ribonucleotide.

In some embodiments, the number of contiguous non-naturally-occurring nucleotides is between 1 and 20.

In some embodiments, the non-naturally-occurring nucleotides comprise phosphorothioated bases.

In some embodiments, the target length range is between 18 and 24 base pairs.

In some embodiments, the first and second adaptor oligonucleotides each further comprise a primer binding site.

One provided method of enriching for short DNA sequences from a mixture of a plurality of DNA sequences comprises providing a population of any of the previously described polynucleotides, contacting the population with the Type IIS or Type III restriction enzyme under reaction conditions sufficient to form a mixture of cleaved polynucleotides and intact polynucleotides, and subsequently enriching for intact polynucleotides.

In some embodiments, the population of polynucleotides is formed by providing a sample comprising a population of RNA molecules having an RNA 5' end and an RNA 3' end; attaching a first linker oligonucleotide, comprising a first linker oligonucleotide sequence and a first linker oligonucleotide 3' end, to the RNA 3' end of the RNA molecules, and attaching a second linker oligonucleotide to the RNA 5' end of the RNA molecules, such that hybrid RNA molecules are formed having the structure as set forth below:
5'—second linker oligonucleotide—RNA molecule—first linker oligonucleotide—3'.

The method further comprises forming first strand cDNA molecules, comprising a first strand cDNA sequence and a first strand cDNA 3' end, from the hybrid RNA molecules by extending a first reverse transcription primer in a template-dependent manner using the hybrid RNA as a template. The first reverse transcription primer is configured to anneal to the first linker oligonucleotide proximate to the first linker oligonucleotide 3' end. The method further comprises forming second strand cDNA molecules from the first strand cDNA molecules by extending a second reverse transcription primer in a template-dependent manner using the first strand cDNA as a template. The second reverse transcription primer is configured to anneal to the first strand cDNA sequence proximate to the first strand cDNA 3' end. This forms double stranded cDNA molecules comprising the first strand cDNA sequence and the second strand cDNA sequence; wherein (a) the first linker oligonucleotide comprises a recognition sequence for a Type IIS or Type III restriction enzyme and the second reverse transcription primer comprises a number of contiguous non-naturally-occurring nucleotides, or (b) the second linker oligonucleotide comprises a recognition sequence for a Type IIS or Type III restriction enzyme and the first reverse transcription primer comprises a number of contiguous non-naturally-occurring nucleotides. The number of contiguous non-naturally-occurring nucleotides incorporated into the first or second reverse transcription primer is sufficient to block cleavage by the type III or Type IIS restriction enzyme if the double stranded cDNA molecule was formed from an RNA molecule having a length within a target length range but does not block cleavage by the Type III or Type IIS restriction enzyme if the double stranded cDNA molecule was formed from an RNA molecule having a length less than the minimum of the target length range or more than the maximum of the target length range.

In some embodiments, the enriching comprises amplifying the intact polynucleotides.

In some embodiments, the first and second adaptor oligonucleotides each further comprise a primer binding site for amplification. The enriching further comprises amplifying the intact polynucleotides by extending a forward PCR primer and a reverse PCR primer. The forward and reverse PCR primers are configured to anneal to the primer binding sites of the first and second adaptor oligonucleotides.

One provided reaction mixture comprises a population of any of the previously described polynucleotides and a Type IIS or Type III restriction enzyme.

DEFINITIONS

Figure 1:
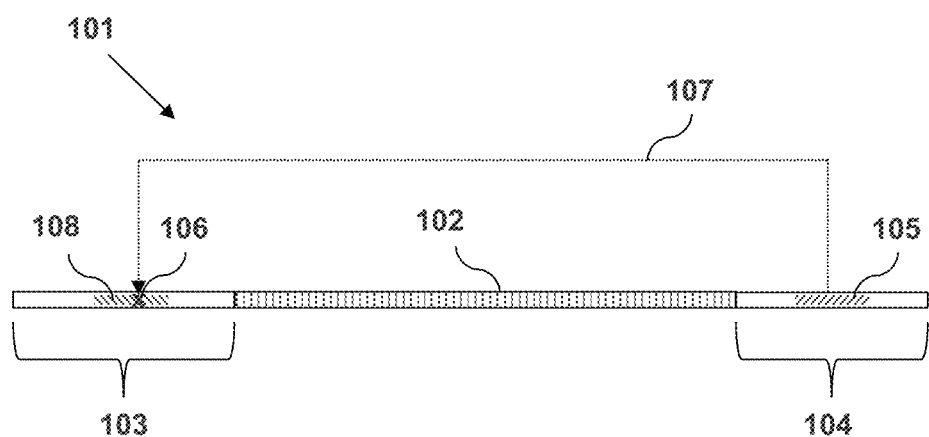
FIG. 1 illustrates a polynucleotide in accordance with an embodiment.

As used herein, the following terms have the meanings ascribed to them unless specified otherwise.

The term "polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Thermally stable polymerase," as used herein, refers to any enzyme that catalyzes polynucleotide synthesis by addition of nucleotide units to a nucleotide chain using DNA or RNA as a template and has an optimal activity at a temperature above 45° C.

The term "nucleic acid amplification" or "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step. PCR can be performed as end-point PCR (i.e., only monitored at an end point) or as quantitative PCR (monitored in "real time").

An "olignucleotide primer" or "primer" refers to an oligonucleotide sequence that anneals to a sequence on a target nucleic acid and serves as a point of initiation of nucleic acid synthesis. Primers can be of a variety of lengths and are often less than 50 nucleotides in length, for example 12-30 nucleotides in length. The length and sequences of primers for use in PCR can be designed based on principles known to those of skill in the art; see, e.g., Innis et al., supra.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs).

The term "hybrid RNA" refers to an RNA molecule that is ligated to one or more linker or adapter sequences.

The terms "linker" and "adapter" refer to nucleotide sequences that are attached to another sequence of DNA or RNA. The linker or adapter can be single-stranded or double-stranded. The linker or adapter can comprise both single- and double-stranded regions. The linker or adapter can comprise RNA nucleotides. The linker or adapter can comprise DNA nucleotides. The linker or adapter can comprise both RNA and DNA nucleotides. The linker or adapter can comprise non-naturally-occurring nucleotides.

The terms "first" and "second" when used herein with reference to adapters, linkers, recognition sites, cleavage sites, binding sites, primers, or other elements are simply to more clearly distinguish the two elements and are not intended to indicate order.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

DETAILED DESCRIPTION

II. Introduction

The inventor has discovered methods, materials, and kits for enriching for polynucleotides of a certain desired size range by using restriction enzymes that cleave at a distance from their recognition sequences (e.g., Type IIS and Type III restriction enzymes). For example, the inventor has discovered that DNA molecules in a mixture can each be linked between a pair of adaptor oligonucleotides wherein one adaptor has a recognition sequence for the restriction enzyme, and the other adaptor has a region of non-naturally occurring nucleotides that cannot be cleaved. If the original DNA molecule linked between the adaptor pair has a size within a certain desired range, then the restriction enzyme will target a cleavage site within the region of non-natural nucleotides. In this case, the enzyme will be unable to cut at the cleavage site, and the construct will remain intact. On other hand, if the original DNA molecule is longer or shorter than the desired size range, then the restriction enzyme will target a cleavage site outside of the region of non-naturally occurring nucleotides. In this case, the enzyme will be able to cut at the cleavage site, and the construct will be digested into two fragments. By subsequently enriching the subpopulation of intact constructs from among the entire construct population, one can then generate a mixture enriched in the polynucleotides having a certain desired size range.

FIG. 1 illustrates one embodiment as a descriptive example. Shown is a DNA construct polynucleotide 101 that comprises a DNA sequence 102, a first adaptor oligonucleotide 103, and a second adaptor oligonucleotide 104. The second adaptor oligonucleotide 104 comprises a recognition site 105 for a restriction enzyme that cleaves DNA at a cleavage site 106 that is a distance 107 from the recognition site. The cleavage site is not determined by a particular sequence of nucleotides but instead is determined as being a particular distance from the enzyme recognition sequence. The first adaptor oligonucleotide 103 comprises a region 108 of contiguous non-naturally-occurring nucleotides that cannot be cleaved by the restriction enzyme. If the length of the DNA sequence 102 within the polynucleotide 101 is such that the cleavage site 106 is within the region 108 of non-naturally-occurring nucleotides, then the polynucleotide will not be cleaved when contacted with the restriction enzyme.

As the cutting distance 107 of the restriction enzyme is a fixed length or range of lengths determined by the choice of restriction enzyme, the position of the cleavage site 106 relative to that of the blocking region 108 will depend on several properties of the polynucleotide 101. These include the number of contiguous non-naturally-occurring nucleotides within the region 108, the location of the region 108 within the first adaptor oligonucleotide 103, the location of the restriction enzyme recognition site 105 within the second adaptor oligonucleotide 104, and the length of the DNA sequence 102. If the sequences of the first and second adaptor oligonucleotides are held constant and the DNA sequence 102 is allowed to vary, then it is the length of the DNA sequence, and whether that length is within a target length range, that will determine whether or not the cleavage site 106 lies within the region 108 of non-naturally-occurring nucleotides.

Figure 2:
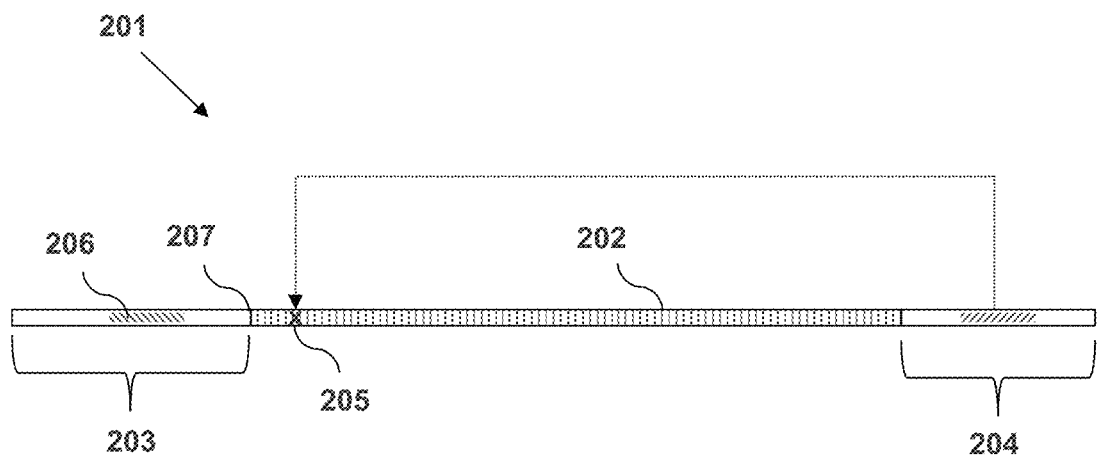
FIG. 2 illustrates a polynucleotide in accordance with an embodiment.

FIG. 2 illustrates an alternative embodiment in which cleavage is not blocked because the DNA sequence is longer than a target length range. Shown is a polynucleotide 201 that comprises a DNA sequence 202, a first adaptor oligonucleotide 203, and a second adaptor oligonucleotide 204. In this example, the cleavage site 205 of a restriction enzyme is not within the region 206 of non-naturally-occurring nucleotides. As a result, cleavage can occur when the polynucleotide 201 is contacted with the restriction enzyme. In the embodiment depicted in FIG. 2, the cleavage site 205 is within the DNA sequence 202. Cleavage would also occur if the cleavage site 205 was within the first adaptor oligonucleotide 203 at a location between the blocking region 206 and the junction 207 of the first adaptor oligonucleotide 203 and the DNA sequence 202.

Figure 3:
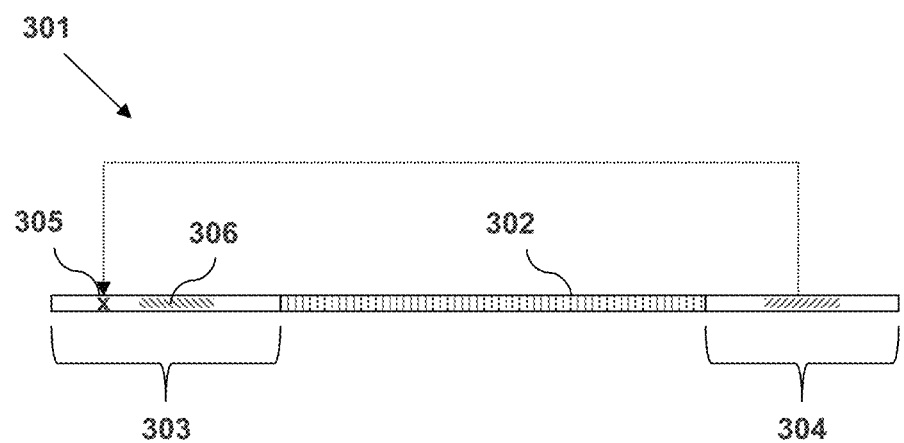
FIG. 3 illustrates a polynucleotide in accordance with an embodiment.

FIG. 3 illustrates an alternative embodiment in which cleavage is not blocked because the DNA sequence is shorter than a target length range. Shown is a polynucleotide 301 that comprises a DNA sequence 302, a first adaptor oligonucleotide 303, and a second adaptor oligonucleotide 304. In this example, the cleavage site 305 of a restriction enzyme is within the first adaptor oligonucleotide 303 but is not within the region 306 of non-naturally-occurring nucleotides. As noted above, the cleavage site if not determined by the sequence but rather is a function of the distance (number of nucleotides) from the recognition sequence. As a result, cleavage can occur when the polynucleotide 301 is contacted with the restriction enzyme.

II. Methods

Methods of enriching for polynucleotides comprising DNA sequences of certain lengths are provided. In some embodiments, a population of polynucleotides is provided, wherein the polynucleotides each comprise a DNA sequence, a first adaptor oligonucleotide comprising a number of contiguous non-naturally-occurring nucleotides, and a second adaptor oligonucleotide comprising a recognition site for a Type IIS or Type III restriction enzyme. The first and second adaptor oligonucleotides can be linked (e.g., introduced by ligation or amplification) to opposite ends of the DNA sequence, and the number of contiguous non-naturally-occurring nucleotides is sufficient to block cleavage by the Type IIS or Type III restriction enzyme if the DNA sequence has a length (not longer or shorter) within a target length range. The population of polynucleotides is contacted with the Type IIS or Type III restriction enzyme under reaction conditions sufficient to form a mixture of cleaved polynucleotides and intact polynucleotides. For example, if the DNA inserted between the first and second adaptor oligonucleotides is either longer or shorter (e.g., as shown in FIGS. 2 and 3, respectfully), then the polynucleotide will be cleaved. If the DNA sequence between the adaptor oligonucleotides is of an appropriate length then the restriction enzymes will not be able to cut the polynucleotide because the non-naturally-occurring contiguous nucleotides will be positioned to block cleavage. Subsequently, the sub-population of intact polynucleotides is enriched from the mixture. In some embodiment, enrichment comprises amplifying the polynucleotides in the mixture using a pair of primers based at or near the ends of the polynucleotides (e.g., designed to hybridize to the first and second adaptor oligonucleotides or their complements, as appropriate, such that intact polynucleotides are amplified whereas cleaved polynucleotides are not. This will result in an enrichment of intact polynucleotides over cleaved polynucleotides.

The DNA sequence can be one sequence among a larger population, mixture or library of DNA sequences. In some embodiments, the various DNA sequences are a mixture of cDNA molecules. In some embodiments, the DNA sequences are a mixture of genomic DNA fragments.

In some embodiments, the first and second adaptor oligonucleotides are attached to opposite ends of the DNA sequence. In some embodiments, the adaptors are attached through primer extension (e.g., amplification). In some embodiments, the adaptors are attached through ligation. The adaptors can contain polymerase chain reaction (PCR) primer binding sites, sequencing primer binding sites, barcode sequences, or other sequences useful for amplifying, quantifying, or identifying the polynucleotide construct.

The number of contiguous non-naturally occurring nucleotides within the first adaptor oligonucleotide can be, for example, from 1 to 20, from 1 to 10, from 5 to 14, from 8 to 17, from 11 to 20, from 1 to 7, from 5 to 10, from 8 to 13, from 11 to 16, from 15 to 20, or more than 20. In some embodiments, the non-naturally-occurring nucleotides are located adjacent to the junction of the first adaptor oligonucleotide and the DNA sequence. In some embodiments, the first adaptor oligonucleotide contains one or more other nucleotides between the junction and the contiguous non-naturally-occurring oligonucleotides.

The contiguous non-naturally-occurring nucleotides are selected based on their ability to decrease (or block) the cleavage efficiencies of Type IIS or Type III restriction enzymes. In this way, these nucleotide analogs protect the polynucleotide construct from enzymatic digestion. In some embodiments, the non-naturally-occurring nucleotides comprise 2'-O-methyl bases. In some embodiments, the non-naturally-occurring nucleotides comprise 2'-fluoro bases. In some embodiments, the non-naturally-occurring nucleotides comprise phosphorothioated bases. The chirality of the phosphorous atoms of the internucleotide linkages among phosphorothioated bases can affect the degree of protection the non-naturally-occurring nucleotides give to the polynucleotide. The $S_p$ stereoisomer of this linkage provides significantly more cleavage inhibition than the $R_p$ stereoisomer. Because a region of phosphorothioated bases can comprise an equal number of each linkage chirality, the presence of 6 or more contiguous bases in the blocking region can increase the overall blocking efficiency of the region.

The Type IIS or Type III restriction enzyme can be selected based on its ability to cleave polynucleotides at a cleavage site that is separate from the recognition site of the restriction enzyme. The restriction enzyme can cleave double-stranded DNA to create a blunt end, a 5'-overhang, or a 3'-overhang. The distance between the recognition site and the cleavage site can be less than 5 base pars, from 5 to 10 base pairs, from 10 to 15 base pairs, from 15 to 20 base pairs, from 20 to 25 base pairs, from 25 to 30 base pairs, from 5 to 15 base pairs, from 10 to 20 base pairs, from 15 to 25 base pairs, from 20 to 30 base pairs, from 5 to 20 base pairs, from 15 to 30 base pairs, or more than 30 base pairs. In some embodiments, the restriction enzyme recognition site is located adjacent to the junction of the second adaptor oligonucleotide and the DNA sequence. In some embodiments, the second adaptor oligonucleotide contains one or more other nucleotides between the junction and the restriction enzyme recognition site.

In some embodiments, the restriction enzyme can be EcoP15I. The recognition site for EcoP15I has the nucleotide sequence 5'-CAGCAG on one of the two complementary DNA strands. Cleavage with EcoP15I typically occurs 25 base pairs away from the recognition site in the 5' to 3' direction and 27 base pairs away from the recognition site on the complementary DNA strand. Cleavage with EcoP15I creates a 5'-NN overhang. In some embodiments, EcoP15I cuts DNA at a distance of 24, 25, 26, 27, or 28 base pairs away from the recognition site in the 5' to 3' direction.

Figure 4:
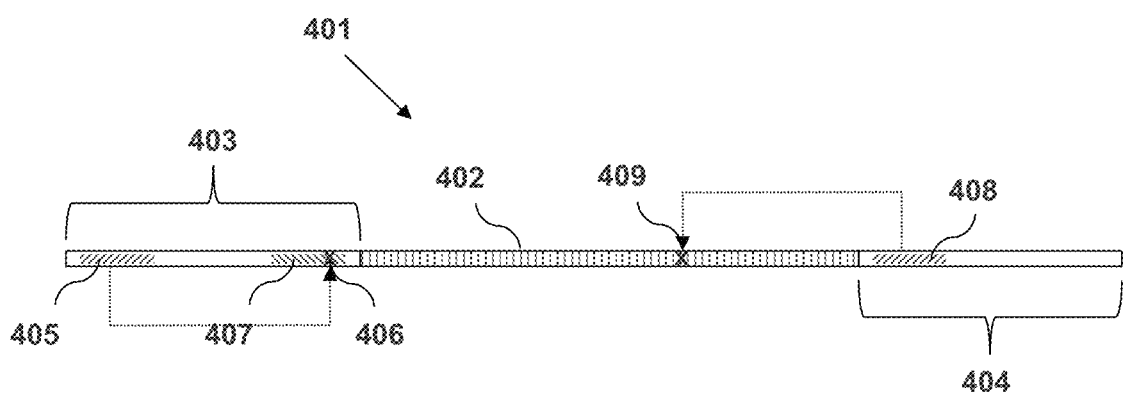
FIG. 4 illustrates a polynucleotide in accordance with an embodiment.

In some embodiments, both the first and second adaptor sequence contain restriction enzyme recognition sites. In some embodiments, the two recognition sites are located on opposite adaptor sequences in a head-to-head orientation. In some embodiments, the recognition sites are recognized by EcoP15I. The efficiency of cleavage by EcoP15I can be improved by the presence of a second, inversely oriented EcoP15I recognition site. (See, e.g., Moncke-Buchner, Elisabeth, Maja Rothenberg, Stefanie Reich, Katja Wagenführ, Hideo Matsumura, Ryohei Terauchi, Detlev H. Krüger, and Monika Reuter. *Journal of Molecular Biology* 387.5 (2009): 1309-1319.) As long as the two restriction sites are located on the same DNA molecule, the cleavage efficiency improvement is independent of the distance between the two recognition sites. (See, e.g., Meisel, Andreas, Thomas A. Bickle, Detlev H. Krüger, and Cornelia Schroeder. *Nature* 355.6359 (1992): 467-469.) It has also been shown that show that cleavage occurs at only one of the two possible cleavage positions of an interacting pair of target sequences. (See, e.g., Mücke, Merlind, Stefanie Reich, Elisabeth Möncke-Buchner, Monika Reuter, and Detlev H. Krüger. *Journal of Molecular Biology* 312.4 (2001): 687-698.) The second EcoP15I recognition site can be positioned such that its cutting length is located in the protecting region of non-naturally-occurring nucleotides FIG. 4 illustrates an embodiment in which both the first and second adaptor sequences have EcoP15I recognition sites in a head-to-head configuration. Shown is a DNA construct polynucleotide 401 that comprises a DNA sequence 402, a first adaptor oligonucleotide 403, and a second adaptor oligonucleotide 404. The first adaptor oligonucleotide 403 comprises a first EcoP15I recognition site 405 corresponding to a first cleavage site 406 that is 24-28 base pairs from the first EcoP15I recognition site. In the embodiment shown in FIG. 4, the first adaptor oligonucleotide 403 further comprises a region 407 of contiguous non-naturally-occurring nucleotides that cannot be cleaved by EcoP15I. The second adaptor oligonucleotide 404 comprises a second EcoP15I recognition site 408 corresponding to a second cleavage site 409 that is 24-28 base pairs from the second EcoP15I recognition site. The cleavage sites are not determined by a particular sequence of nucleotides but instead are determined as each being a particular distance in the 3' directions from one of the restriction enzyme recognition sequences.

In the embodiment illustrated in FIG. 4, the region 407 of non-naturally-occurring nucleotides will prevent cleavage originating from a first EcoP15I enzyme bound to the first recognition site 405 on the first adaptor sequence 403. This blockage at the first cleavage site 406 will occur independent of the length of the insert DNA sequence 402 attached to the first 403 and second 404 adaptor oligonucleotides. The first EcoP15I enzyme can still influence the cleavage efficiency of a second EcoP15I enzyme bound to the second recognition site 408. As described above, the ability of this second EcoP15I enzyme to cleave the polynucleotide construct will depend in part upon the length of the insert DNA sequence 402. In the embodiment shown in FIG. 4, the DNA sequence 402 has a length long enough so that the second cleavage site 409 is not within the blocking region 407, and cleavage of the polynucleotide construct 401 can occur.

The polynucleotide can be configured such that cleavage is blocked, as shown in the example of FIG. 1, if the insert DNA sequence is within a target length range. In this case, the cleavage site is located within the region of contiguous non-naturally-occurring nucleotides. The target length range can be, for example, from 7 to 22 base pairs, from 14 to 29 base pairs, from 21 to 36 base pairs, from 7 to 17 base pairs, from 10 to 20 base pairs, from 13 to 23 base pairs, from 16 to 26 base pairs, from 19 to 29 base pairs, from 22 to 32 base pairs, from 26 to 36 base pairs, from 7 to 12 base pairs, from 10 to 15 base pairs, from 13 to 18 base pairs, from 16 to 21 base pairs, from 19 to 24 base pairs, from 22 to 27 base pairs, from 25 to 30 base pairs, from 18 to 33 base pairs, or from 31 to 36 base pairs. In some embodiments, the target length range is from 19 to 24 base pairs.

In one embodiment, a first adaptor oligonucleotide comprises a region of 6 contiguous phosphorothioated bases located adjacent to and 3' of the junction of the first adaptor oligonucleotide and the DNA sequence. In this embodiment, a second adaptor oligonucleotide comprises an EcoP15I recognition sequence adjacent to the junction of the second adaptor oligonucleotide and the DNA sequence. Because the EcoP15I restriction enzyme typically cleaves DNA at a distance of 25 base pairs removed from the recognition site in the 3' direction, this polynucleotide construct is configured to block cleavage by EcoP15I if the inserted DNA sequence has a length within a target range of from 19 to 24 base pairs. In the case of a 19-base-pair DNA sequence, the blocking region of the polynucleotide would comprise phosphorothioated bases located 20 to 25 base pairs away from the restriction enzyme recognition site, encompassing the EcoP15I cleavage site. In the case of a 24-base-pair DNA sequence, the blocking region of the polynucleotide would comprise phosphorothioated bases located 25 to 30 base pairs away from the restriction enzyme recognition site, again encompassing the EcoP15I cleavage site. In the case of a DNA sequence length less than the 19-base-pair minimum of the target length range, the end of the blocking region farthest from the restriction enzyme recognition site would be less than 25 base pairs away from the recognition site, and EcoP15I cleavage would not be blocked. In the case of a DNA sequence greater than the 24-base pair maximum of the target, the end of the blocking region closest to the restriction enzyme recognition site would be greater than 25 base pairs away from the recognition site, and EcoP15I would not be blocked.

If the region of 6 contiguous phosphorothioated bases of the above example was instead located on the complementary strand, and the region was 2 base pairs removed from the junction, then similar results would be seen. This is because the EcoP15I restriction enzyme typically cleaves DNA at a distance of 27 base pairs removed from the recognition site on the complementary strand in the 3' direction. This polynucleotide construct would then be configured to block cleavage by EcoP15I if the inserted DNA sequence has a length within a target range of from 19 to 24 base pairs. In the case of a 19-base-pair DNA sequence, the blocking region of the polynucleotide would comprise phosphorothioated bases located 22 to 27 base pairs away from the restriction enzyme recognition site, encompassing the EcoP15I cleavage site. In the case of a 24-base-pair DNA sequence, the blocking region of the polynucleotide would comprise phosphorothioated bases located 27 to 32 base pairs away from the restriction enzyme recognition site, again encompassing the EcoP15I cleavage site. In the case of a DNA sequence length less than the 19-base-pair minimum of the target length range, the end of the blocking region farthest from the restriction enzyme recognition site would be less than 27 base pairs away from the recognition site, and EcoP15I cleavage would not be blocked. In the case of a DNA sequence greater than the 24-base pair maximum of the target, the end of the blocking region closest to the restriction enzyme recognition site would be greater than 27 base pairs away from the recognition site, and EcoP15I would not be blocked.

In some embodiments, the polynucleotide construct comprises one restriction enzyme recognition site as described above. In some embodiments, the polynucleotide construct can comprise two or more restriction enzyme recognition sites. The multiple recognition sites can be located on one or both of the first and second adaptor oligonucleotides. The multiple recognition sites can have identical or different sequences, and can be recognized by one or multiple Type IIS or Type III restriction enzymes. In some embodiments, two or more recognition sites located on one of the first or second adaptor oligonucleotide can be recognized by Type IIS or Type III restriction enzymes that can cleave the polynucleotide at two or more cleavage sites located on the opposite adaptor oligonucleotide. In some embodiments, one or more recognition sites located on the first adaptor oligonucleotide can be recognized by a Type IIS or Type III restriction enzyme that can cleave the polynucleotide at one or more cleavage sites located on the second adaptor oligonucleotide, and one or more recognition sites located on the second adaptor oligonucleotide can be recognized by a Type IIS or Type III restriction enzyme that can cleave the polynucleotide at one or more cleavage sites located on the first adaptor oligonucleotide.

In some embodiments comprising two or more restriction enzyme recognition sites, the polynucleotide construct can further comprise two or more regions of contiguous non-naturally-occurring nucleotides. These blocking regions can be configured to have lengths and positions sufficient to block cleavage of the polynucleotide if the polynucleotide is contacted with the Type IIS or Type III restriction enzymes that recognize the two or more restriction enzyme recognition sites. The polynucleotide construct can also comprise one or more regions of contiguous non-naturally occurring nucleotides configured to have lengths and positions sufficient for a single blocking region to prevent cleavage by two or more Type IIS or Type III restriction enzymes in contact with the polynucleotide.

One or both of the first and second adaptor oligonucleotides can further comprise one or more primer binding sites. The primer binding sites can be located on one of either the first or second adaptor oligonucleotides, or they can be located on both the first and second adaptor oligonucleotides. In some cases, a primer, or portion thereof, can bind or hybridize to a primer binding site if the primer or primer portion comprises at least 6, 8, 10, 12, 14, 16, or 18 contiguous oligonucleotides that are together complementary to a sequence of the primer binding site. The contiguous oligonucleotides can also comprises "universal" nucleotides that are complementary to more than one nucleotide partner. Alternatively, a primer, or portion thereof, can hybridize to a primer binding site if there are fewer than 1 or 2 complementary mismatches over at least 12, 14, 16, or 18 contiguous complementary nucleotides.

In some cases, the primer binding sites are PCR primer binding sites. In some embodiments, the first oligonucleotide adaptor comprises a forward PCR primer binding site and the second oligonucleotide adaptor comprises a reverse PCR primer binding site. In some embodiments, the first oligonucleotide adaptor comprises a reverse PCR binding site and the second oligonucleotide adaptor comprises a forward PCR primer site. The PCR primer binding sites can be configured to enable the generation of DNA amplification product molecules that each comprise the insert DNA sequence, under conditions sufficient for carrying out a PCR amplification reaction comprising PCR primers that hybridize to the forward and reverse PCR primer binding sites.

Figure 5:
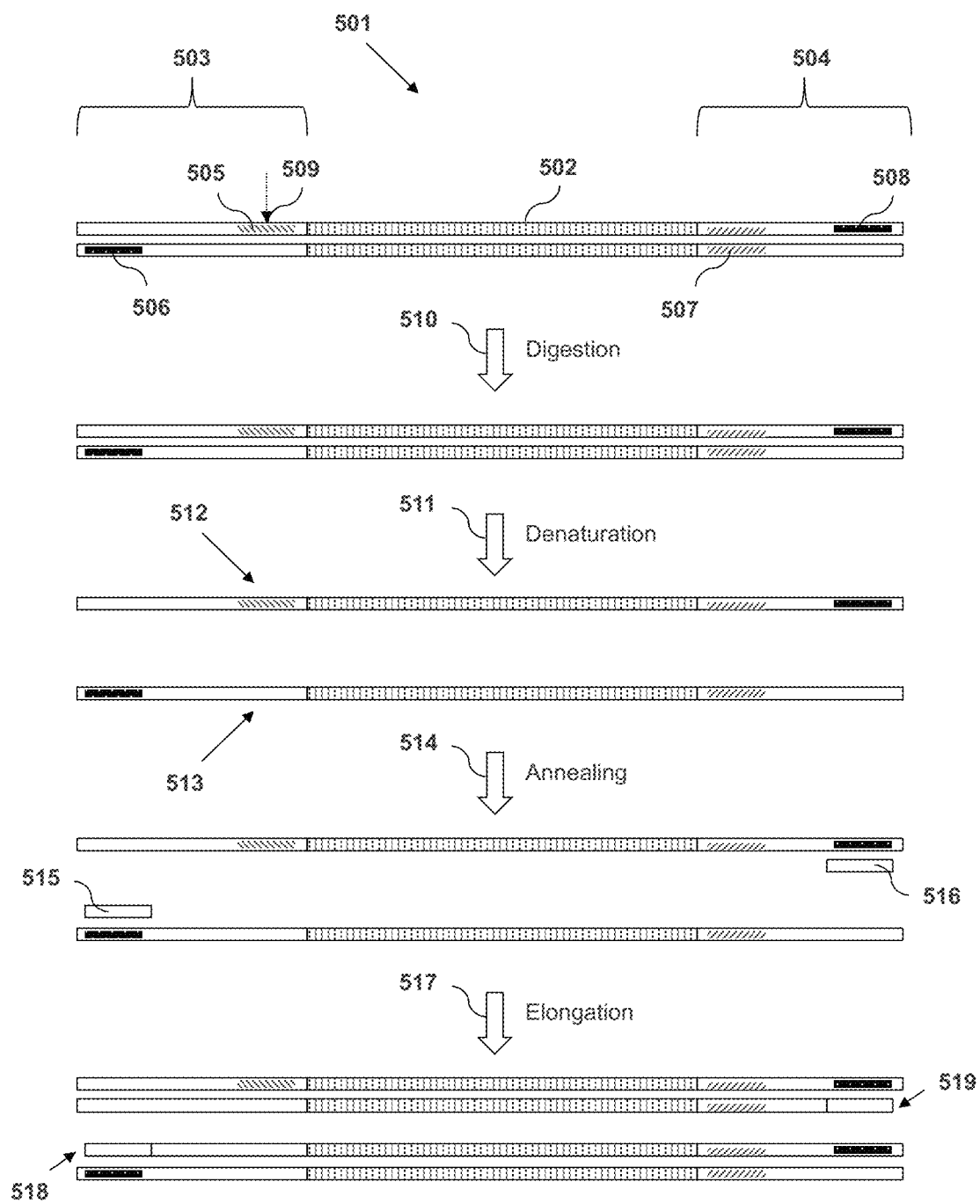
FIG. 5 illustrates amplification of a polynucleotide in accordance with an embodiment.

FIG. 5 illustrates an embodiment in which an insert DNA sequence has a length within a target length range, cleavage by restriction enzyme is blocked, and amplification of the DNA sequence can occur. Shown in the figure is a double-stranded polynucleotide 501 comprising a DNA sequence 502, a double-stranded first adaptor oligonucleotide 503, and a double-stranded second adaptor oligonucleotide 504. The first adaptor oligonucleotide comprises a region 505 of contiguous non-naturally-occurring nucleotides, and a first PCR primer binding site 506. The second adaptor oligonucleotide 504 comprises a recognition site 507 for a Type IIS or Type III restriction enzyme, and a second PCR primer binding site 508. Because the DNA sequence 502 has a length within the target length range, the cleavage site 509 for a restriction enzyme that recognizes the restriction site 507 is within the blocking region 505. As a result, if the polynucleotide 501 is contacted with the restriction enzyme in a digestion step 510, digestion of the polynucleotide does not occur. A subsequent denaturation step 511 can then separate the two strands 512 and 513 of the polynucleotide. In an annealing step 514, a first PCR primer 515 can hybridize with the first PCR primer binding site, and a second PCR primer 516 can hybridize with the second PCR primer binding site. An elongation step 517 can then be used to create new complementary DNA strands 518 and 519. These new complementary DNA strands 518 and 519 can then anneal to form a new copy of the original DNA sequence 501. In view of this elongation, amplification of intact polynucleotides occurs, resulting in enrichment compared to other polynucleotides (e.g., those discussed below) in the mixture that are cleaved and thus not amplified to the same extent.

Figure 6:
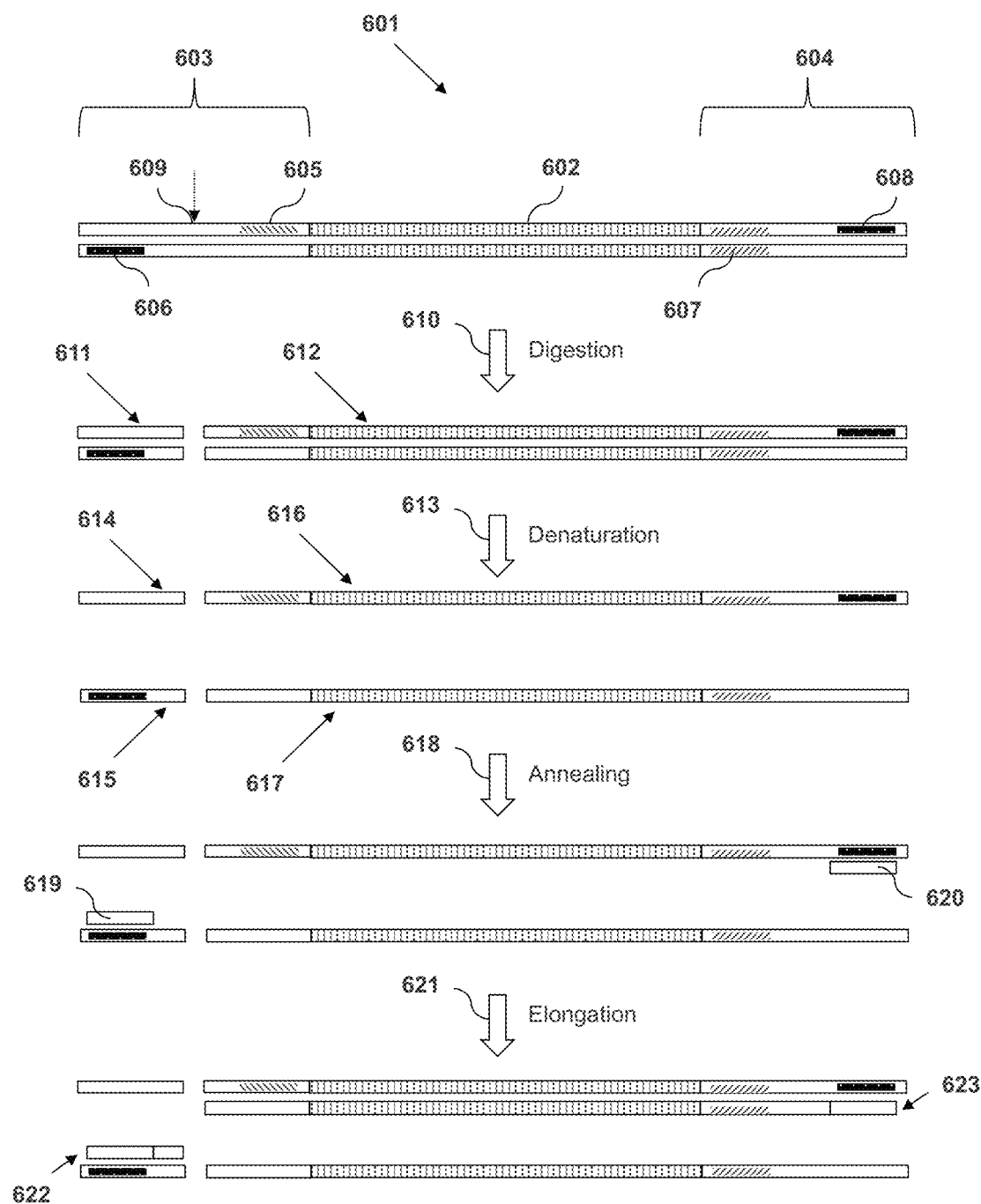
FIG. 6 illustrates prevention of amplification of a polynucleotide in accordance with an embodiment.

FIG. 6 illustrates an embodiment in which an insert DNA sequence has a length outside of a target length range, cleavage by restriction enzyme is not blocked, and amplification of the DNA sequence cannot occur. Shown in the figure is a double-stranded polynucleotide 601 comprising a DNA sequence 602, a double-stranded first adaptor oligonucleotide 603, and a double-stranded second adaptor oligonucleotide 604. The first adaptor oligonucleotide comprises a region 605 of contiguous non-naturally-occurring nucleotides, and a first PCR primer binding site 606. The second adaptor oligonucleotide 604 comprises a recognition site 607 for a Type IIS or Type III restriction enzyme, and a second PCR primer binding site 608. Because the DNA sequence 602 has a length outside the target length range, the cleavage site 609 for a restriction enzyme that recognizes the restriction site 607 is outside the blocking region 605. As a result, if the polynucleotide 601 is contacted with the restriction enzyme in a digestion step 610, the enzyme digests the polynucleotide into two double-stranded DNA fragments 611 and 612. A subsequent denaturation step 613 can then separate each of fragments 611 and 612 into two strands, generating four strands 614, 615, 616, and 617. In an annealing step 618, a first PCR primer 619 can hybridize with the first PCR primer binding site, and a second PCR primer 620 can hybridize with the second PCR primer binding site. An elongation step 621 can then be used to create new DNA strands 622 and 623. Because these new DNA strands 622 and 623 are not complementary to one another, and do not both contain regions identical to entire length of the original DNA sequence 602, they cannot then anneal to form a new copy of the original DNA sequence. Therefore, successful amplification of the cleaved polynucleotide is not possible. While FIGS. 5 and 6 are depicted separately, the initial mixture of polynucleotides can include polynucleotides of desired and undesired lengths resulting in a mixture of the polynucleotides depicted in FIGS. 5 and 6 and enrichment of the polynucleotides as depicted in FIG. 5 as a result of their amplification.

One or both of the first and second adaptor oligonucleotides can further comprise one or more capture regions. The capture regions can be any sequence in which the reverse complement thereof is capable of capturing or hybridizing to a target polynucleotide or a plurality of polynucleotides of interest. In some cases the capture region of the reverse complement comprises one or more inosine, nitroindole, or other universal nucleotides. In some embodiments, the capture regions comprise biotinylated nucleotides.

One or both of the first and second adaptor oligonucleotides can further comprise one or more barcode regions used to identify the polynucleotide that contains the adaptor or adaptors. The barcode regions can each contain at least 1, 2, 3, 4, 5, 6, 7, 8, 9, 10, 11, 12, 13, 14, 15, 16 17, 18, 19, 20, 21, 22, 23, 24, 25, 26, 27, 28, 29, 30, 31, 32, 33, 34, or 35 barcode nucleotides. For example, a barcode region of 20 nucleotides can be used to uniquely identify $4^{20}$ polynucleotides. In some cases, the barcode regions can each contain from 5 to 25 barcode nucleotides, from 8 to 20 barcode nucleotides, or from 10 to 14 barcode nucleotides.

In addition to containing sequences complementary to the first and second PCR primer binding sites, one or both of the PCR primer can also contain one or more sequences that function as further binding sites, capture regions, capture regions, or barcode regions. The PCR primers or adaptor oligonucleotides can further contain any additional sequences needed for any desired downstream application. Non-limiting examples of these applications include RNA sequencing (RNA-seq), real-time PCR or quantitative PCR (qPCR), microarrays, or biomarker detection.

In some embodiments, the insert DNA sequence is a cDNA generated from the reverse transcription of an RNA molecule. In some embodiments, DNA are cDNAs generated from a mixture of RNA molecules. The mixture of RNA molecules can be of a single type of RNA molecules, or of two or more types of RNA molecules. The RNA molecules can be coding RNA or noncoding RNA. The RNA molecules can be, for example, messenger RNA (mRNA), ribosomal RNA (rRNA), signal recognition particle RNA (SRP RNA), transfer RNA (tRNA), transfer-messenger RNA (tmRNA), guide RNA (gRNA), SmY RNA, small Cajal body-specific RNA (scaRNA), ribonuclease P (RNase P), ribonuclease MRP (RNase MRP), Y RNA, telomerase RNA component (TERC), spliced leader RNA (SL RNA), antisense RNA (aRNA), cis-natural antisense transcript (cis-NAT), CRISPR RNA (crRNA), and small interfering RNA (siRNA). The RNA molecules can be fragments of any one or more types of RNA.

The RNA molecules can be small noncoding RNA molecules including, but not limited to miRNA, snRNA, snoRNA, piRNA, or lncRNA. MicroRNAs (miRNAs), typically 18 or 19 to 25 nt in length, are non-protein-coding RNAs that can inhibit the translation of target mRNAs (see, e.g., Croce and Calin, *Cell* 122(1): 6-7 (2005)). Other small RNAs include small nucleoplasmic RNAs (snRNAs) and small nucleolar RNAs (snoRNAs). These small RNA molecules can function, for example, in mRNA splicing (U1, U2, and U4 to U6 snRNAs), mRNA and rRNA processing (U7 snRNA; U3 and U8 snoRNAs), and site selection for RNA modification by methylation of the 2' hydroxyl group (box C/D snoRNAs) or by pseudouridine formation (box H/ACA snoRNAs). Piwi-interacting RNAs (piRNAs) were identified through association with Piwi proteins in mammalian. piRNAs can range from 26-30 nucleotides in length. Long noncoding RNA (lncRNA) have also been described.

Also provided are methods for forming a population of DNA sequences from the reverse transcription of a mixture of RNA molecules. In some embodiments, a sample comprising a population of RNA molecules is provided, wherein the RNA molecules have an RNA 5' end and an RNA 3' end. In some embodiments, a first linker oligonucleotide, comprising a first linker oligonucleotide sequence and a first linker oligonucleotide 3' end, is attached to the RNA 3' end of the RNA molecules, and a second linker oligonucleotide is attached to the RNA 5' end of the RNA molecules, such that hybrid RNA molecules are formed. Subsequently, first strand cDNA molecules can be formed from the hybrid RNA molecules by extending a first reverse transcription primer in a template-dependent manner using the hybrid RNA as a template. The cDNA molecules comprise a first strand cDNA sequence and a first strand cDNA 3' end, and the first reverse transcription primer is configured to anneal to the first linker oligonucleotide proximate to the first linker oligonucleotide 3' end. Second strand cDNA molecules can then be formed from the first strand cDNA molecules by extending a second reverse transcription primer in a template-dependent manner using the first strand cDNA as a template, thereby forming double stranded cDNA molecules comprising the first strand cDNA sequence and the second strand cDNA sequence. The second reverse transcription primer can be configured to anneal to the first strand cDNA sequence proximate to the first strand cDNA 3' end. Also, either (a) the first linker oligonucleotide can comprise a recognition sequence for a Type IIS or Type III restriction enzyme and the second reverse transcription primer can comprise a number of contiguous non-naturally-occurring nucleotides, or (b) the second linker oligonucleotide can comprise a recognition sequence for a Type IIS or Type III restriction enzyme and the first reverse transcription primer can comprise a number of contiguous non-naturally-occurring nucleotides. The number of contiguous non-naturally-occurring nucleotides incorporated into the first or second reverse transcription primer can be sufficient to block cleavage by the type III or Type IIS restriction enzyme if the double stranded cDNA molecule was formed from an RNA molecule having a length within a target length range but to not block cleavage by the Type III or TypeIIS restriction enzyme if the double stranded cDNA molecule was formed from an RNA molecule having a length less than the minimum of the target length range or more than the maximum of the target length range.

The attachment of the first linker or adaptor oligonucleotide to the RNA molecule can be formed in a ligation reaction. In some embodiments, the ligation reaction is catalyzed by the activity of an RNA Ligase 2 enzyme. The RNA Ligase 2 can be T4 RNA Ligase 2. T4 RNA Ligase 2 catalyzes the formation of phosphodiester bonds between the 5'-phosphate end of the first linker and the 3'-hydroxyl end of the RNA molecule in a reaction that requires ATP as a cofactor.

In some embodiments, the ligation of the first linker oligonucleotide to the DNA sequence is catalyzed by T4

RNA Ligase 2, Deletion Mutant. This enzyme is also known as T4 RNA Ligase 2, truncated or Rnl2 (1-249), and contains the first 249 amino acids of the full-length T4 RNA Ligase 2. In these embodiments, the 5' end of the first linker is pre-adenylated and the 3' end of the first linker is blocked by, for example a —NH₃ group, prior to the ligation reaction. The ligation reaction does not require ATP as a cofactor. Because the deletion mutant is unable to adenylated the 5' end of a substrate, only those linkers that have been pre-adenylated at their 5' end can be ligated to the 3'-hydroxyl end of the RNA sequence. This results in a reduction of background ligation. T4 RNA Ligase 2, Deletion Mutant has been used for optimized linker ligation for the cloning of miRNA for RNA-seq library construction.

The attachment of the second linker or adaptor oligonucleotide to the 5' end of the RNA molecule can be formed in a ligation reaction. In some embodiments, the ligation reaction is catalyzed by the activity of an RNA Ligase 1 enzyme. The RNA Ligase 1 can be T4 RNA Ligase 1. T4 RNA Ligase 1 catalyzes the formation of a phosphodiester bond between the 5'-phosphate end of the RNA molecule and the 3'-hydroxyl end of the second linker in a reaction that requires ATP as a cofactor.

Figure 7:
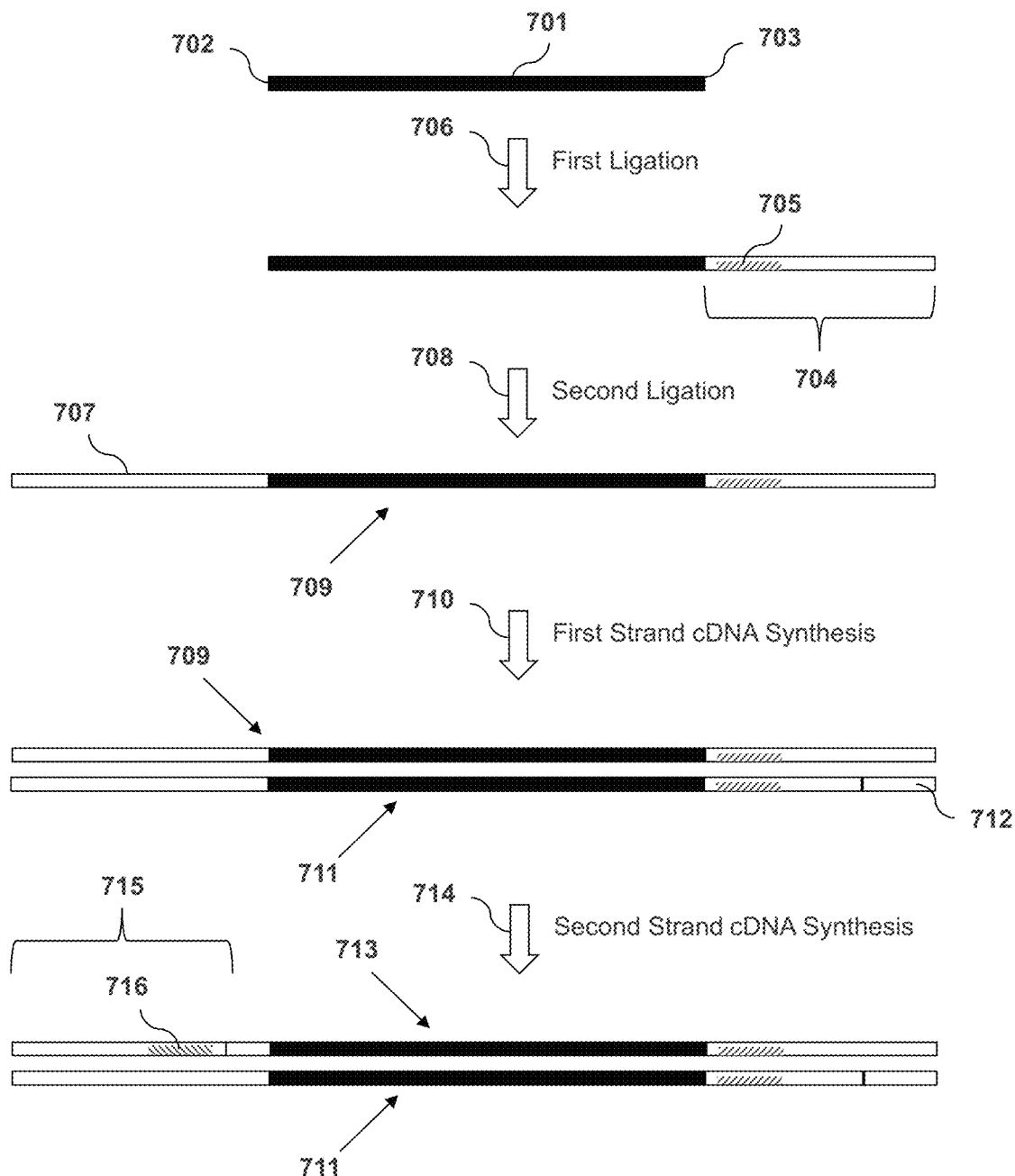
FIG. 7 illustrates the formation of a polynucleotide in accordance with an embodiment.

FIG. 7 illustrates an embodiment in which the DNA sequence is formed from the reverse transcription of an RNA molecule transcription. Shown is an RNA sequence 701 having a 5' end 702 and a 3' end 703. A first linker oligonucleotide 704 comprising a recognition sequence 705 for a Type IIS or Type III restriction enzyme is attached the 3' end 703 of the RNA sequence 701 in a first ligation step 706. A second linker oligonucleotide 707 is then attached to the 5' end 702 of the RNA sequence 701 in a second ligation step 708. Alternatively, the second linker oligonucleotide 707 can be attached to the RNA sequence 701 prior to the attachment of the first adaptor oligonucleotide 704. In either case, the result is the formation of a hybrid RNA molecule 709 having the structure:

5'—second linker oligonucleotide—RNA molecule—first linker oligonucleotide—3'

First strand cDNA 711 is then formed in a first strand cDNA synthesis step 710 by annealing a first reverse transcription primer 712 to the hybrid RNA 709 proximate to its 3' end, and then extending the primer in a template-dependent manner using the hybrid RNA molecule as a guide. Second strand cDNA 713 is subsequently formed in a second strand cDNA synthesis step 714 by annealing a second reverse transcription primer 715 to the first strand cDNA 711 proximate to its 3' end, and then extending the primer in a template-dependent manner using the first strand cDNA as a guide. The second reverse transcription primer 715 can comprise a region 716 of contiguous non-naturally-occurring nucleotides. In this way, the two cDNA strands combine to form a polynucleotide construct comprising (a) a DNA sequence reverse transcribed from an original RNA sequence, (b) a number of contiguous non-naturally-occurring nucleotides, and (c) a recognition site for a Type IIS or Type III restriction enzyme. The region of non-naturally-occurring nucleotides is on the opposite side of the DNA sequence than the restriction enzyme recognition site, and the number and position of non-naturally-occurring nucleotides in the region is block cleavage by the restriction enzyme if the original RNA sequence has a length within a target length range.

Figure 8:
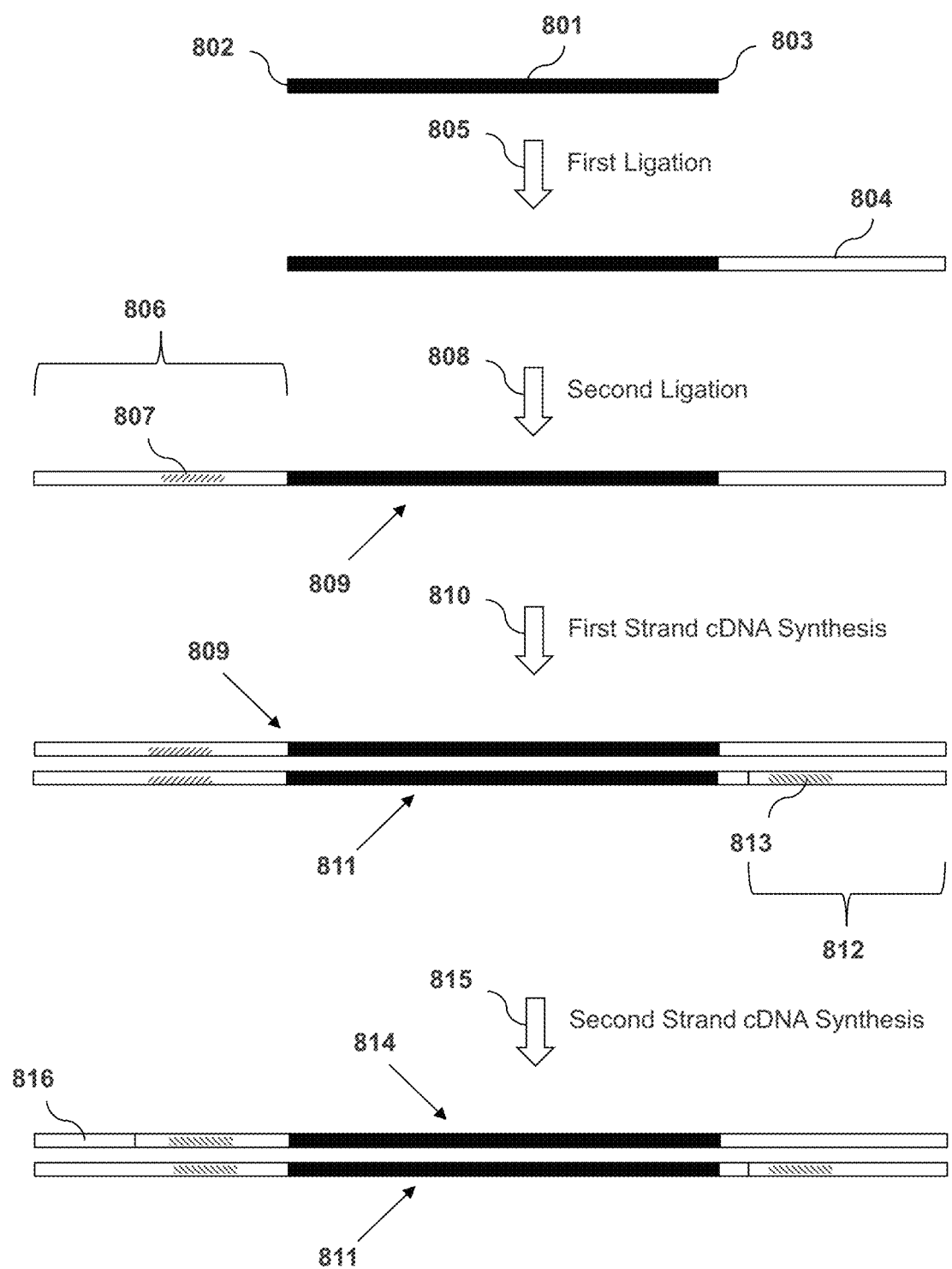
FIG. 8 illustrates the formation of a polynucleotide in accordance with an embodiment.

FIG. 8 illustrates an alternate embodiment in which the DNA sequence is formed from the reverse transcription of an RNA molecule transcription. Shown is an RNA sequence 801 having a 5' end 802 and a 3' end 803. A first linker oligonucleotide 804 is attached the 3' end 803 of the RNA sequence 801 in a first ligation step 706. A second linker oligonucleotide 806 comprising a recognition sequence 807 for a Type IIS or Type III restriction enzyme is then attached to the 5' end 802 of the RNA sequence 801 in a second ligation step 808. Alternatively, the second linker oligonucleotide 806 can be attached to the RNA sequence 801 prior to the attachment of the first adaptor oligonucleotide 804. In either case, the result is the formation of a hybrid RNA molecule 809 having the structure:

5'—second linker oligonucleotide—RNA molecule—first linker oligonucleotide—3'

First strand cDNA 811 is then formed in a first strand cDNA synthesis step 810 by annealing a first reverse transcription primer 812 to the hybrid RNA 809 proximate to its 3' end, and then extending the primer in a template-dependent manner using the hybrid RNA molecule as a guide. The first reverse transcription primer 812 can comprise a region 813 of contiguous non-naturally-occurring nucleotides. Second strand cDNA 814 is subsequently formed in a second strand cDNA synthesis step 815 by annealing a second reverse transcription primer 816 to the first strand cDNA 811 proximate to its 3' end, and then extending the primer in a template-dependent manner using the first strand cDNA as a guide. In this way, the two cDNA strands combine to form a polynucleotide construct comprising (a) a DNA sequence reverse transcribed from an original RNA sequence, (b) a number of contiguous non-naturally-occurring nucleotides, and (c) a recognition site for a Type IIS or Type III restriction enzyme. The region of non-naturally-occurring nucleotides is on the opposite side of the DNA sequence than the restriction enzyme recognition site, and the number and position of non-naturally-occurring nucleotides in the region is block cleavage by the restriction enzyme if the original RNA sequence has a length within a target length range.

Any of a variety of reverse transcriptases can be used to reverse transcribe the RNA molecule to the first strand cDNA. Exemplary reverse transcriptases include but are not limited to murine leukemia virus (MLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H⁻ reverse transcriptases. In additional embodiments, a DNA polymerase that functions as an RNA polymerase can be used. For example, Tth and Z05, which are DNA polymerases, can function as reverse transcriptase in the presence of manganese. The concentration of the reverse transcriptase can vary and optimal concentrations can be determined empirically and depend on the particular reverse transcriptase used.

In some embodiments, the second linker adaptor is attached through the method of template switching. (See, e.g., U.S. Pat. No. 5,962,271.) In this method, a first cDNA synthesis primer is annealed to an RNA molecule proximate to the 3' end of the RNA molecule. The first synthesis primer is extended in a template-dependent manner using the RNA molecule as a template. When the reverse transcriptase enzyme catalyzing the primer extension reaches the 5' end of the RNA molecule, the enzyme switches templates such that an adaptor oligonucleotide serves as a template extension. In some embodiments, this adaptor oligonucleotide comprises a region of contiguous non-naturally occurring nucleotides.

In some embodiments, the adaptor oligonucleotide comprises a recognition sequence for a Type IIS or Type III restriction enzyme.

Figure 9:
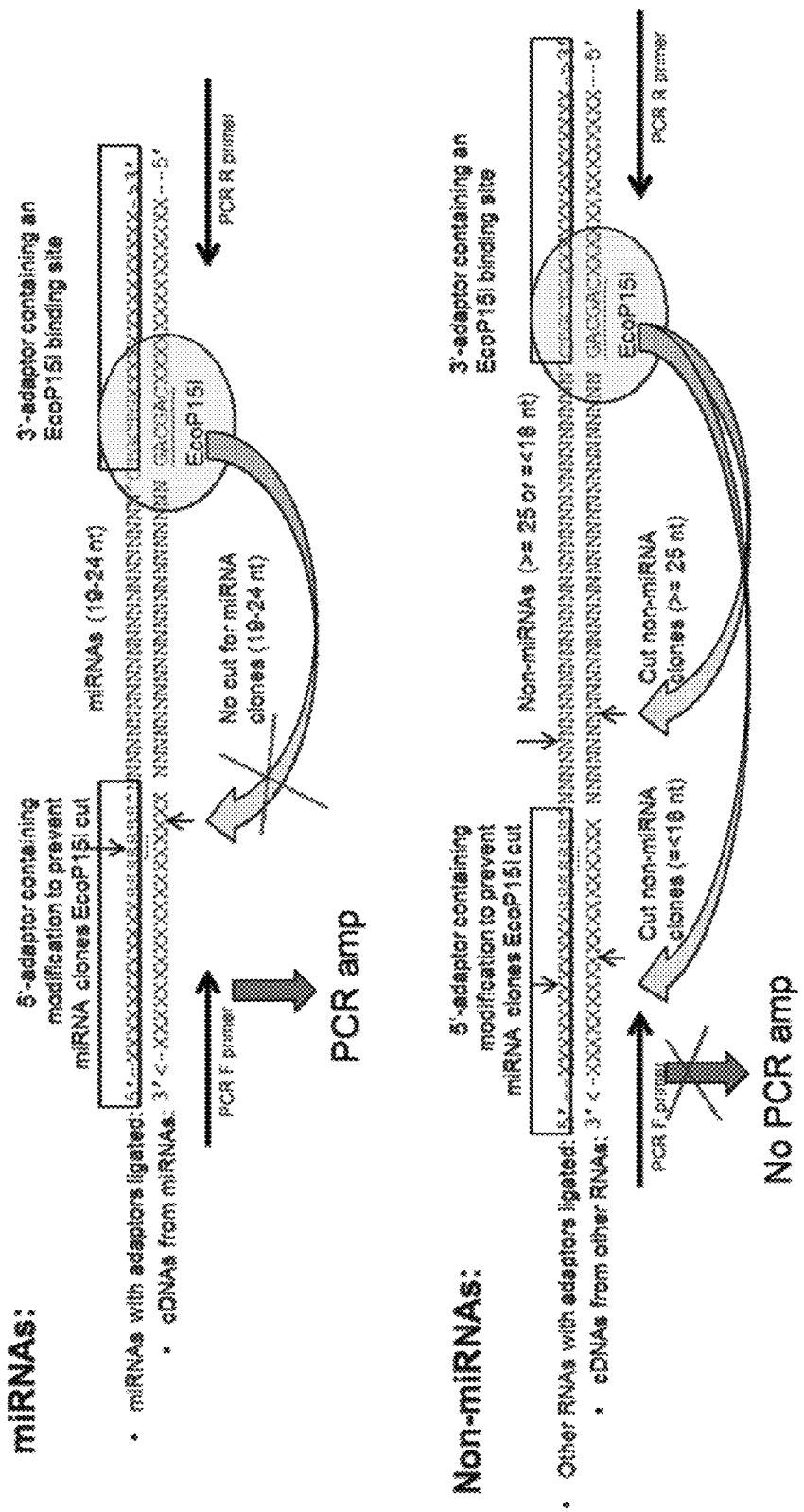
FIG. 9 illustrates a polynucleotide in accordance with an embodiment. In both the upper and lower polynucleotides, the 3'-adaptor containing an EcoP15I binding site is SEQ ID NO:1. The reverse complement of the adaptor, containing EcoP15I, is SEQ ID NO:2.

FIG. 9 illustrates an embodiment for enriching miRNA molecules from a mixed population of RNA molecules. The upper polynucleotide in FIG. 9 shows an example of an miRNA molecule serving as the sequence source for the DNA insert between a 5' adaptor and a 3' adaptor. The lower polynucleotide in FIG. 9 shows an example of a non-miRNA molecule serving as the sequence source for the DNA insert between a 5' adaptor and a 3' adaptor. The 3' adaptors contain EcoP15I binding sites, and the 3' adaptors contain modified bases capable of preventing clones constructed with miRNA molecules from being cut by the action of an EcoP15I restriction enzyme. In the case of the upper polynucleotide constructed with miRNA having a length of 19-24 nucleotides, the polynucleotide is not cleaved. This intact polynucleotide can then be amplified through PCR using a PCR forward primer that recognizes a portion of the 5' adaptor, and a PCR reverse primer that recognizes a portion of the 3' adaptor. In the case of the lower polynucleotide constructed from a non-miRNA having a length greater than 25 nucleotides or less than 19 nucleotides, the polynucleotide can be cleaved. This cleaved polynucleotide then cannot be amplifies through PCR using the PCR forward and reverse primers as the 5' adaptor and the 3' adaptor will no longer be part of the same molecule. The result of cleavage and amplification then will be a population of polynucleotides that is enriched for those members derived from miRNA molecules.

After the intact polynucleotides have been enriched from a mixture of intact and cleaved polynucleotides, the enriched population may be used in one or more downstream processes familiar to a person of ordinary skill in the art. As non-limiting examples, the enriched population can be subjected to microarray hybridization, RNA-seq or next-generation sequencing, qPCR or real-time PCR, library construction, subtractive hybridization, amplification, or the creation of assay probes The polynucleotides can be present in libraries, mixtures, or populations of a plurality of polynucleotides. In some embodiments, the polynucleotides each comprise one of a population of cDNA molecules that have been cloned into adaptors. The cDNA molecules can be generated from the reverse transcription of a mixed population of RNA. In some embodiments, the mixed populations of RNA, cDNA or polynucleotides have at least 10, at least 100, at least 500, at least 1000, at least 2000, at least 3000, at least 4000, at least 5000, at least 6000, at least 7000, at least 8000, at least 9000, at least 10,000, or more than 10,000 different sequences among the population members.

The RNA mixture can be a sample derived from one or more organisms. The sample can be from a single cell. The sample can be from two or more cells. The cells can be of the same or different species. The RNA sample can be from a bacterial source. The RNA sample can be from a viral source. The RNA sample can be from a mammalian source.

III. Kits

Also provided are kits for enriching short polynucleotide sequences from a sample. The kits can contain any combination of reagents as described elsewhere herein. In some embodiments, the kit comprises a Type IIS or Type III restriction enzyme and a first adaptor oligonucleotide. The first adaptor oligonucleotide can comprises a number of contiguous non-naturally-occurring nucleotides. The first adaptor oligonucleotide can comprise at least one ribonucleotide. The number of non-naturally-occurring nucleotides can be, for example, from 2 to 20, from 2 to 11, from 5 to 14, from 8 to 17, from 11 to 20, from 2 to 7, from 5 to 10, from 8 to 13, from 11 to 16, from 15 to 20, or more than 20. In some embodiments, the non-naturally-occurring nucleotides are phosphorothiolated bases. In some embodiments, the Type IIS or Type III restriction enzyme is EcoP15I.

The kit can further comprise an RNA ligase. The RNA ligase can be RNA ligase 2. In some embodiments, the RNA ligase is T4 RNA Ligase 2, Deletion Mutant or T4 RNA Ligase 2, Truncated. The kit can further comprise an RNase inhibitor. The kit can further comprise a ligation reaction buffer. The buffer can contain one or more buffer components and salts. In some embodiments, the buffer component is Tris-HCl. In some embodiments, the salts are KCl and $MgCl_2$.

In some embodiments, the kit comprises a second adaptor oligonucleotide. The second adaptor oligonucleotide can comprise a recognition sequence for a Type IIS or Type III restriction enzyme. In some embodiments, the Type IIS or Type III restriction enzyme is EcoP15I. The kit can further comprise a second RNA ligase. In some embodiments, the second RNA ligase is T4 RNA Ligase 1. The kit can further comprise ATP.

In some embodiments, the kit further comprises a first reverse transcription primer. The kit can further comprise a second reverse transcription primer. One of the first or second reverse transcription primers can either comprise a region of non-naturally-occurring nucleotides, or be complementary to a region of non-naturally-occurring nucleotides that is on the first or second adaptor oligonucleotide. The kit can further comprise a reverse transcriptase. The kit can further comprise a Type IIS or Type III restriction enzyme. In some embodiments, the Type IIS or Type III restriction enzyme is EcoP15I.

In some embodiments, the kit further comprises a forward PCR primer and a reverse PCR primer. The forward and reverse PCR primers can be configured to selectively anneal to PCR primer binding sequences of or complementary to the first and second adaptor oligonucleotides, or of or complementary to the first and second reverse transcription primers. The kit can further comprise a thermostable DNA polymerase. In some embodiments, the DNA polymerase is Taq DNA polymerase or iProod DNA polymerase. The kit can further comprise a mixture of dNTPs and a PCR reaction buffer.

IV. Example

The following example is provided in order to better enable one of ordinary skill in the art to make and use the disclosed compositions and methods, and is not intended to limit the scope of the invention in any way.

Figure 10:
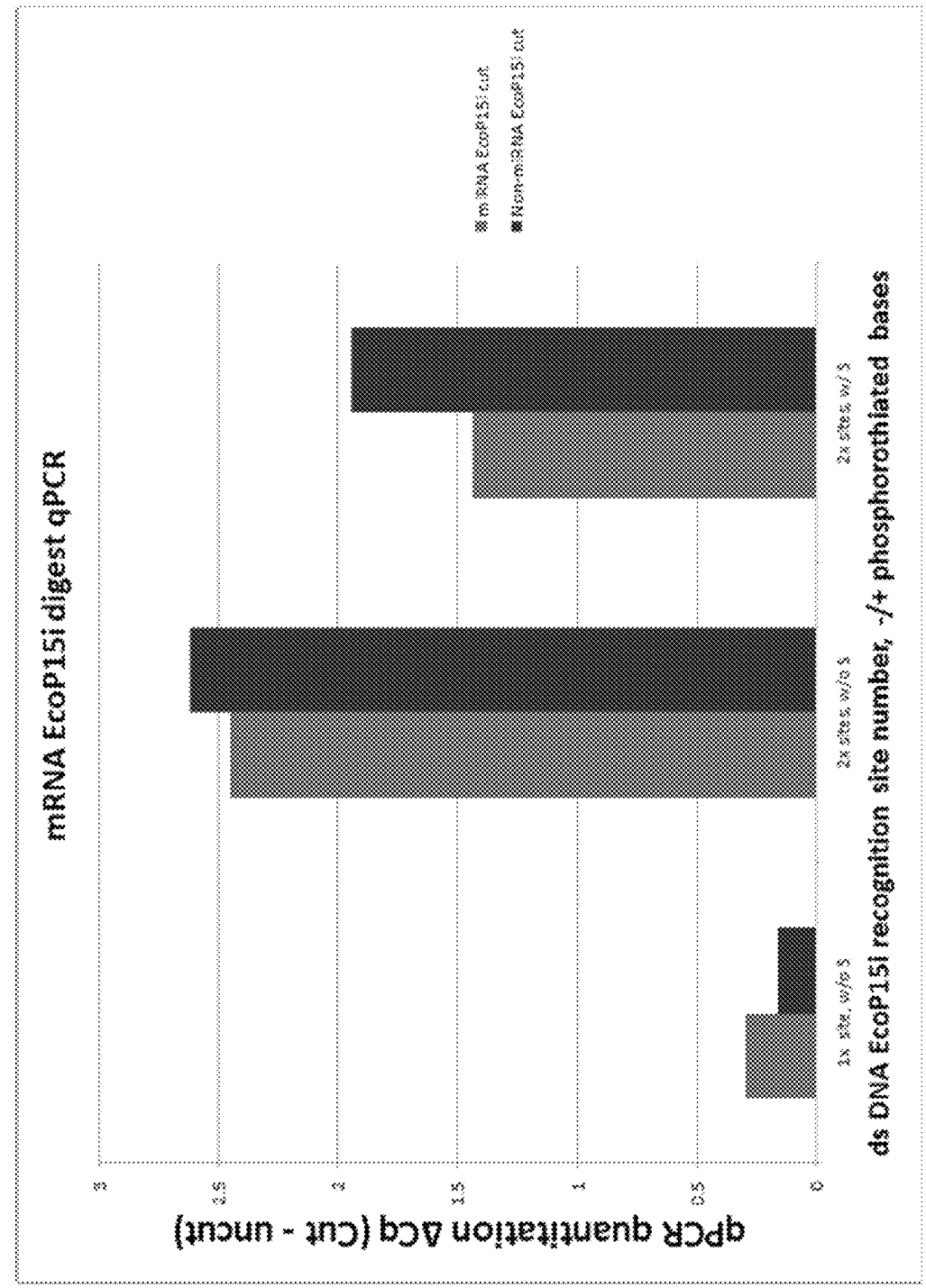
FIG. 10 is a graph of the effects of restriction enzyme recognition site numbers, phosphorothioated bases, and RNA insert sizes on EcoP15i polynucleotide digestion.

FIG. 10 presents results from the digestion with the Type III restriction enzyme EcoP15i of different populations of polynucleotides. Some of the populations were generated as described above with a single EcoP15i recognition site. Some populations were generated with two EcoP15i recognition sites. From the data shown in FIG. 10, upon exposure to the restriction enzyme, the polynucleotide populations having two EcoP15i recognition sites had much larger percentages cut than the polynucleotide populations having a single recognition site. These results demonstrate the improved cutting efficiency that can be achieved by including a second EcoP15i recognition site within the polynucleotide.

Some of the polynucleotide populations included non-naturally-occurring phosphorothioated bases in the EcoP15i cleavage site. Some of the polynucleotides did not include phosphorothioated bases. From the data shown in FIG. 10, upon exposure to the restriction enzyme, the polynucleotide populations that included two EcoP15i recognition sites and phosphorothioated bases in the cleavage site had smaller percentages cut than the polynucleotide populations having two EcoP15i recognition sites and no phosphorothioated bases. These results demonstrate the ability of the non-naturally occurring phosphorothioated bases to at least partially block the digestion of the polynucleotides by the restriction enzyme.

Some of the polynucleotide populations were generated as described above using miRNA sequences having lengths within the desired target range. Some of the polynucleotide populations were generated as described above using sequences having lengths greater than or less than the desired target range. From the data shown in FIG. 10, for polynucleotide populations having two EcoP15i recognition sites and phosphorothioated bases in the cleavage site, the ability of the phosphorothioated bases to at least partially block EcoP15i digestion was greater for populations generated using miRNA sequences than for populations generated using non-miRNA sequences. These results demonstrate the ability of the provided methods to discriminate between sequence insert sizes, and to preferentially enrich populations having a targeted sequence length.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, websites, and databases cited herein are hereby incorporated by reference in their entireties for all purposes.

---

---

What is claimed is:

1. A polynucleotide comprising
   a DNA sequence,
   a number of contiguous non-naturally-occurring nucleotides located in a first adaptor oligonucleotide, and
   a recognition site for a Type IIS or Type III restriction enzyme,
   wherein the recognition site is located in a second adaptor oligonucleotide,
   wherein the first and second adaptor oligonucleotides are linked to opposite ends of the DNA sequence,
   wherein the number of contiguous non-naturally-occurring nucleotides and the locations of the recognition site and the contiguous non-naturally-occurring nucleotides are selected to block cleavage by the Type IIS or Type III restriction enzyme if the DNA sequence has a length between 18 and 24 base pairs, and
   wherein the non-naturally-occurring nucleotides comprise 6 or more phosphorothioated bases.

2. The polynucleotide of claim 1, wherein the DNA sequence comprises a cDNA.

3. The polynucleotide of claim 1, wherein the Type IIS or Type III restriction enzyme is EcoP15I.

4. The polynucleotide of claim 1, wherein the first or second adaptor oligonucleotides comprises at least one ribonucleotide.

5. The polynucleotide of claim 1, wherein the first and second adaptor oligonucleotides each further comprise a primer binding site.

6. A kit for enriching short polynucleotide sequences from a sample, the kit comprising
a Type IIS or Type III restriction enzyme,
a first adaptor oligonucleotide comprising a number of contiguous non-naturally-occurring nucleotides; and
a second adaptor oligonucleotide comprising a recognition site for the Type IIS or Type III restriction enzyme;
wherein the contiguous non-naturally-occurring nucleotides block cleavage by the Type IIS or Type III restriction enzyme if separated from the second adaptor ogligonucleotide by a nucleotide sequence having a length within a target length range and do not block cleavage by the Type IIS or Type III restriction enzyme if not separated from the second adaptor ogligonucleotide by a nucleotide sequence having a length within the target length range;
wherein the target length range is between 18 and 24 base pairs; and
wherein the non-naturally-occurring nucleotides comprise 6 or more phosphorothioated bases.

7. The kit of claim 6, wherein the kit further comprises a ligase.

8. The kit of claim 6, wherein the Type IIS or Type III restriction enzyme is EcoP15I.

9. The kit of claim 6, wherein the first or second adaptor oligonucleotides comprises at least one ribonucleotide.

10. The kit of claim 6, wherein the first and second adaptor oligonucleotides each further comprise a primer binding site.

11. A method of enriching for short DNA sequences from a mixture of a plurality of DNA sequences, the method comprising,
providing a population of polynucleotides of claim 1,
contacting the population with the Type IIS or Type III restriction enzyme under reaction conditions sufficient to form a mixture of cleaved polynucleotides and intact polynucleotides, and subsequently
enriching for intact polynucleotides.

12. The method of claim 11, wherein the population of polynucleotides is formed by
providing a sample comprising a population of RNA molecules having an RNA 5' end and an RNA 3' end;
attaching a first linker oligonucleotide to the RNA 3' end of the RNA molecules, and attaching a second linker oligonucleotide to the RNA 5' end of the RNA molecules, such that hybrid RNA molecules are formed having the structure as set forth below:

5'—second linker oligonucleotide—RNA molecule—first linker oligonucleotide—3';

forming first strand cDNA molecules, comprising a first strand cDNA sequence and a first strand cDNA 3' end, from the hybrid RNA molecules by extending a first reverse transcription primer in a template-dependent manner using the hybrid RNA as a template, the first reverse transcription primer configured to anneal to the first linker oligonucleotide;

forming second strand cDNA molecules from the first strand cDNA molecules by extending a second reverse transcription primer in a template-dependent manner using the first strand cDNA as a template, the second reverse transcription primer configured to anneal to the first strand cDNA sequence proximate to the first strand cDNA 3' end, thereby forming double stranded cDNA molecules comprising the first strand cDNA sequence and the second strand cDNA sequence; wherein (a) the first linker oligonucleotide comprises a recognition sequence for a Type IIS or Type III restriction enzyme and the second reverse transcription primer comprises a number of contiguous non-naturally-occurring nucleotides, or (b) the second linker oligonucleotide comprises a recognition sequence for a Type IIS or Type III restriction enzyme and the first reverse transcription primer comprises a number of contiguous non-naturally-occurring nucleotides, wherein the number of contiguous non-naturally-occurring nucleotides incorporated into the first or second reverse transcription primer is sufficient to block cleavage by the type III or Type IIS restriction enzyme if the double stranded cDNA molecule was formed from an RNA molecule having a length within a target length range but does not block cleavage by the Type III or Type IIS restriction enzyme if the double stranded cDNA molecule was formed from an RNA molecule having a length less than the minimum of the target length range or more than the maximum of the target length range.

13. The method of claim 11, wherein the enriching comprises amplifying the intact polynucleotides.

14. The method of claim 13, wherein the first and second adaptor oligonucleotides each further comprise a primer binding site for amplification, and wherein the enriching further comprises amplifying the intact polynucleotides by extending a forward PCR primer and a reverse PCR primer, wherein the forward and reverse PCR primers are configured to anneal to the primer binding sites of the first and second adaptor oligonucleotides.

* * * * *